United States Patent [19]

Farrell

[11] Patent Number: 4,895,564
[45] Date of Patent: Jan. 23, 1990

[54] PERCUTANEOUS FEMORAL BYPASS SYSTEM

[76] Inventor: Edward M. Farrell, 66 Dolan Dr., Nepean, Ontario, Canada, K2J 1Z1

[21] Appl. No.: 204,043

[22] Filed: Jun. 8, 1988

[51] Int. Cl.$^4$ .............................................. A61M 5/18
[52] U.S. Cl. .................................................. 604/164
[58] Field of Search .............. 604/164, 165, 166, 170, 604/264, 171

[56] References Cited

U.S. PATENT DOCUMENTS

| | | | |
|---|---|---|---|
| 4,569,347 | 2/1986 | Frisbie | 604/164 X |
| 4,644,936 | 2/1987 | Schiff | 604/165 |
| 4,772,266 | 9/1988 | Gronhong | 604/164 |
| 4,798,193 | 1/1989 | Giesy et al. | 604/164 X |

Primary Examiner—John D. Yasko
Attorney, Agent, or Firm—Pravel, Gambrell, Hewitt, Kimball & Krieger

[57] ABSTRACT

A percutaneous dilator system comprising:
(i) a first dilator tube having a tapered leading end and inwardly directed shoulder means spaced from the trailing end defining a gripping section between the shoulder and the trailing end;
(ii) a bore through the tube dimensioned to receive a guide wire; and
(iii) a second dilator tube having a bore corresponding to the outside diameter of the first tube, a tapered leading end, and an inwardly directed flange at the trailing end dimensioned to note with the shoulder means to limit relative axial mating movement of the first and second tubes while exposing the gripping section;

whereby a puncture through tissue containing a guide wire of predetermined guage may be enlarged without substantial tissue damage by placing the first tube over the guide wire through the puncture, then sliding the second dilator tube over the wire and first dilator tube until its flange means engages the shoulder means to enlarge the puncture further, the dilator tubes being subsequently removable as a unit by pulling on the gripping section.

4 Claims, 14 Drawing Sheets

FIG. IA
FIG. IB
FIG. IC
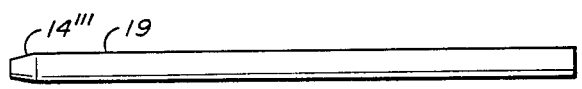
FIG. ID
FIG. 2A
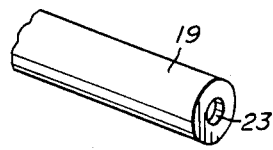
FIG. 2B
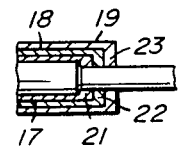
FIG. 2C

PERCUTANEOUS FEMORAL BYPASS SYSTEM

This invention relates to a kit for cannula placement consisting of a system of guide wire dilators, sheath, cannulae, obturators and couplers for human tissue, and in particular for use in percutaneous femoral-femoral bypass systems.

There are many surgical procedures in which it is necessary to perforate tissue and insert a cannula into an internal organ, body cavity or blood vessel. Such systems have particular utility in cardiac support prior to which it is necessary to bypass the heart to maintain circulation of blood through an external circuit. It is common practice to insert a cannula in a vein or artery by making an incision through the tissue above a vein or artery and in the vessel wall, following which a cannula is sewn in place. There is a considerable amount of time necessary, the attendant loss of blood, and a risk of damaging of the vessel wall.

What is required, therefore, is a cannula introducer system with which a tube may be placed in a body cavity, organ or vessel in the least invasive manner while minimizing the loss of fluids, and which can be inserted with relative ease by a skilled technician or physician without the need for the presence of a surgeon.

The present invention, in one aspect, accordingly provides such a system comprising of a series of dilator sleeves of gradually increasing internal and external diameters, which can be progressively inserted over a wire that has been placed into the body within a needle by which an initial, small perforation is made. The dilator sleeves have smoothly tapered tips such that the perforation can be gradually enlarged without risk of tearing of the tissue. The sleeves are flexible and once a perforation of the desired size has been made a sheath can be placed over them; alternatively the sheath can be mounted around the outer sleeve prior to insertion. The innermost sleeve is provided with a shoulder remote from its tip and each progressively larger sleeve has an inwardly directed flange engageable with the shoulder so that removal of the innermost sleeve naturally results in removal of the whole series of sleeves in one movement. Subsequently a cannula having an external diameter corresponding to the internal diameter of the sheath and having its own obturator may be threaded through the sheath over the wire and the cannula eventually coupled to whatever equipment is appropriate to the support process, for example a heart lung machine.

According to another aspect of the invention there is provided a cannula assembly comprising a conventional cannula adapted for threading over a wire, in which there is placed with an interference fit an obturator containing a through bore dimensioned to receive a wire. The obturator may be provided with an air release valve.

According to a third aspect of the invention, there is provided a sleeve normally placed in position with the outer dilator and including a section radially inwardly compressible to act as an obturator.

According to a fourth aspect of the invention, there is provided a kit comprising the components described above packaged for use, for example in an emergency room, in cases where a heart perhaps weakened by a heart attack can be relieved of a portion of its job by use of the kit and an associated pump.

It should be understood that each of the components, especially the dilator kit, is capable of use in other surgical procedures and while the invention is described in the environment of giving access to an artery or vein, it can be used elsewhere, for example in procedures where percutaneous access to the kidney is required or to other internal organs.

The invention will now be described by reference to the accompanying drawings, in which:

FIGS. 1a, b, c and d illustrate a basic dilator set comprising four components;

FIGS. 2a, 2b and c illustrate, respectively, an interlocked dilator system, a detail of one of the dilation sleeves, and a section of the proximal ends of the dilator sleeves, interlocked;

Figure 3:
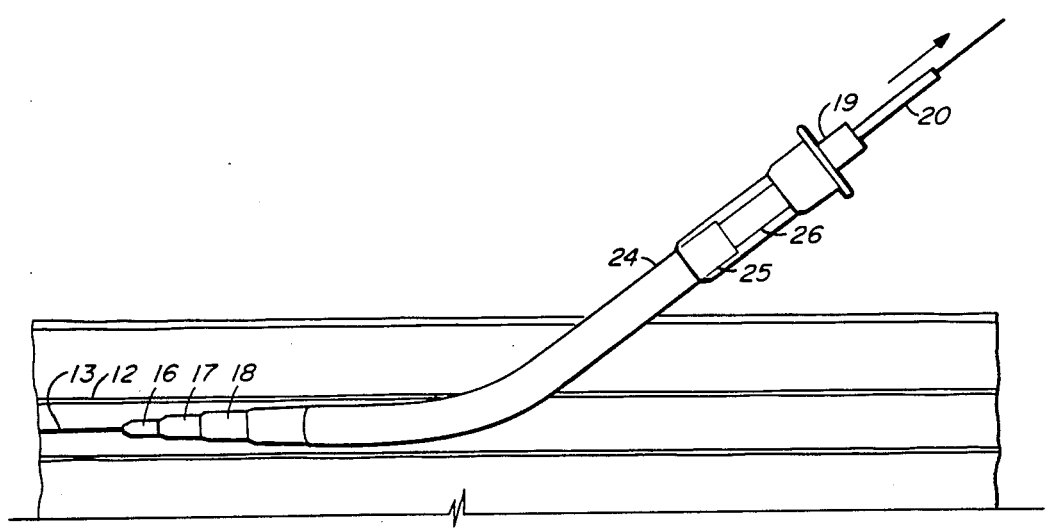
FIG. 3 illustrates the placement of a sheath and final dilator through the skin and subcutaneous tissue into a vein or artery.

FIGS. 5a, 5b 5c and 5d illustrate obturators and details thereof;

FIGS. 6 through 23 illustrate, in order, the steps taken by the physician to implant a percutaneous femoral-femoral by-pass system comprising all of the components illustrated in FIGS. 1 through 5.

THE DILATOR ASSEMBLY

FIG. 1 illustrates a series of four dilator sleeves 16, 17, 18 and 19, each of which has a tip 14, 14′, 14″0 and 14‴ that is tapered gently to facilitate dilation as will be described below. Of particular note is the shoulder 15 and the reduced end portion or tail 20 on dilator 16. Referring to FIG. 2a, the dilators are shown interlocked with dilator 16 threaded through dilator 17, dilator 17 through dilator 18 and dilator 18 through dilator 19. At the end opposite the tips of the dilators, shoulders are provided that are engageable with the shoulder 15 (FIG. 2c) on dilator 16 so that shoulder 21 on dilator 17 engages the shoulder 15 on dilator 16 and so on. Thus, as will be described below once all of the dilators are in place, pulling on the removal tail 20 of dilator 16 will effect immediate removal of all of the dilator tubes as will be described below.

It should be noted that the internal diameter of the dilator 16 closely corresponds to the external diameter of a guide wire 13 (see e.g. FIG. 3) so that leakage of blood between the wire and the dilator does not occur, at least to any appreciable extent. Similarly, each of the dilators is freely but not loosely slidable in relation to its adjacent dilator. The dilator sleeves are formed from a suitable polymeric material.

THE SHEATH AND OBTURATOR

Figure 4:
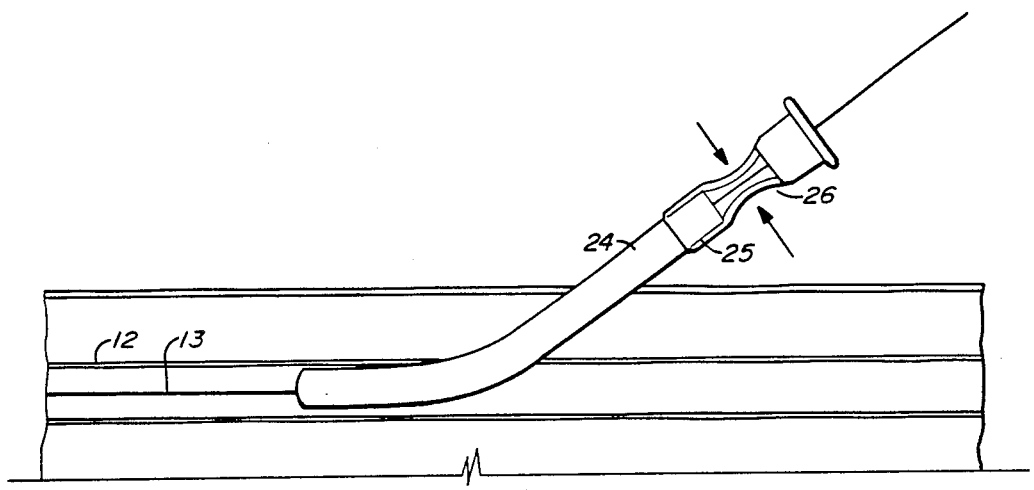
FIG. 4 illustrates the sheath in place over a wire with the obturator portion compressed to prevent the release of blood.

In FIG. 3, as noted above the wire and dilator sleeves are in place in a vein or artery 12. Additionally, there is shown a sheath 24 having an obturator 25 with a portion 26 that is readily compressible. The sheath 24 may be installed after emplacement of the dilator sleeve 16, or may be inserted with it for which purpose the assembly of dilator sleeves prior to emplacement will have the sheath 24 mounted thereon. The compressible portion 26 is shown in FIG. 4 in its compressed state and after removal of the dilator sleeves where, to prevent the loss of blood through the sheath 24 the compressible portion 26 is tightly squeezed over the wire 13 to prevent the loss of blood.

THE CANNULAE

Figure 5A:
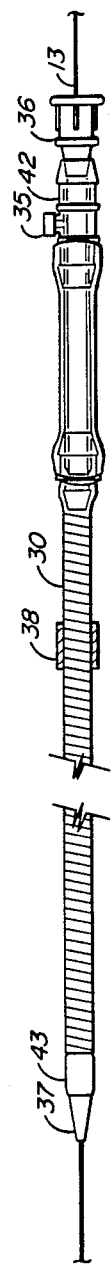
Figure 5B:
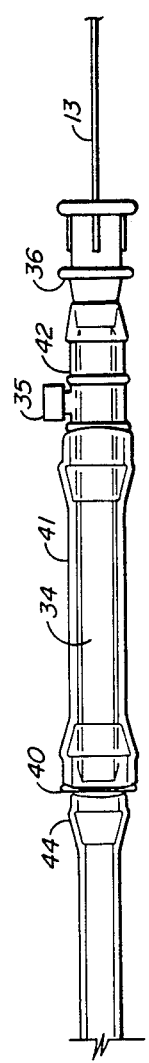

In FIGS. 5a through 5d, cannulae suitable for use with the dilator system described above are illustrated. In FIG. 5a, a cannula 30 having a smooth, rounded leading end 43 and a proximal connecting end 44 is shown threaded over the wire 13. Within the cannula 30 there is an obturator of tubular form 34, with a central bore dimensioned to receive the wire 13. Secured to the proximal end 44 of the cannula 30 is a connector 40 of a type known to those skilled in the art, and likewise an air release valve 42 having a knob 35 is illustrated as secured to the sleeve. A handle element 36 is secured to the proximal end of the obturator 34. It will be noted that distal end 37 of the obturator is smoothly tapered so that when the cannula is passed into a vein or artery or other organ, damage will not occur.

Figure 5C:
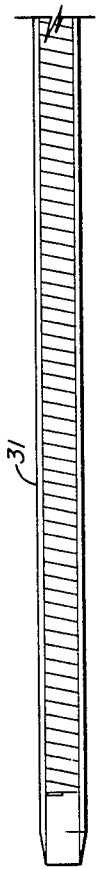
Figure 5D:
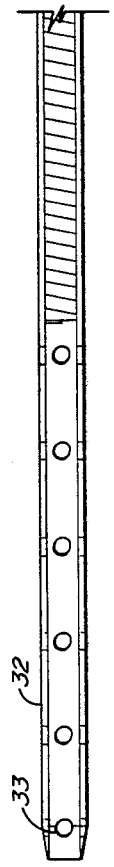

FIG. 5c illustrated a standard tubular arterial cannula tip, and FIG. 5d illustrated a venous drainage cannula tip having perforations 33 extending over a substantial portion of the leading end of the cannula so that if negative pressure is applied at the proximal end of the cannula, there will be less of a tendency for the vein in which displaced to collapse. In FIG. 5a, a sleeve will be noted, slidable along the exterior of the cannula 30, with a slight interference fit. The purpose for the sleeve will be described below.

Referring now to FIGS. 6 through 23, an application for the system described is illustrated. Here, a femoral-femoral by-pass is being installed, for example for cardiac support.

Figure 6:
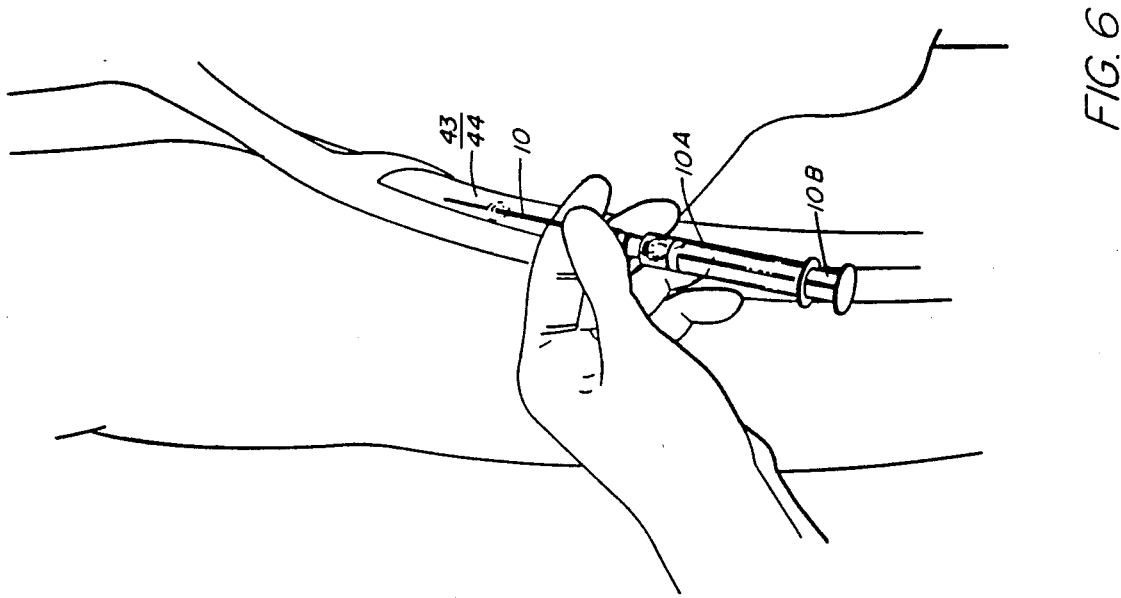

In FIG. 6, syringe 10a is illustrated having mounted to it a needle 10. The needle is being pushed through the skin into the inferior vena cava 44. As is standard in the art, the syringe and needle are operated to withdraw a small amount of blood so that the doctor can ensure that the needle is in the vein 44.

Figure 7B:
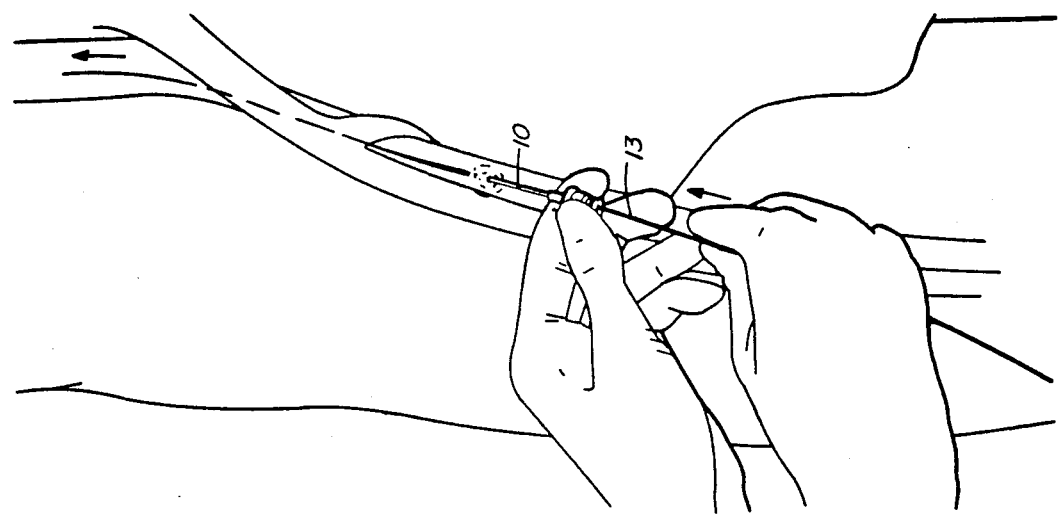

Next, as shown in FIG. 7b, wire 13 is threaded through needle 10 and up into the inferior vena cava toward the heart. The wire acts as a guide for installation of the remaining equipment as described below.

Figure 7A:
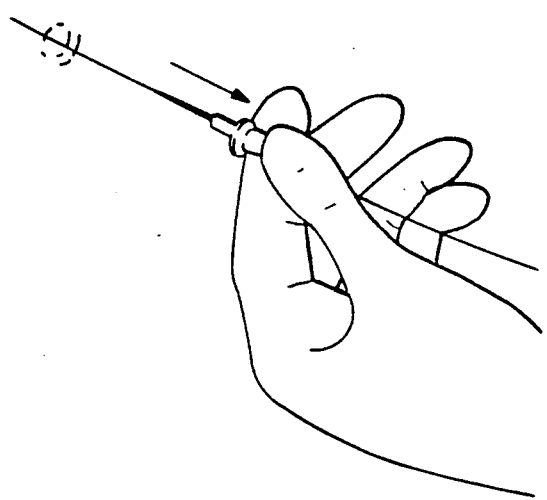

FIG. 7a illustrated the removal of the needle 10 over the wire 13 after the wire is in place.

Figure 8:
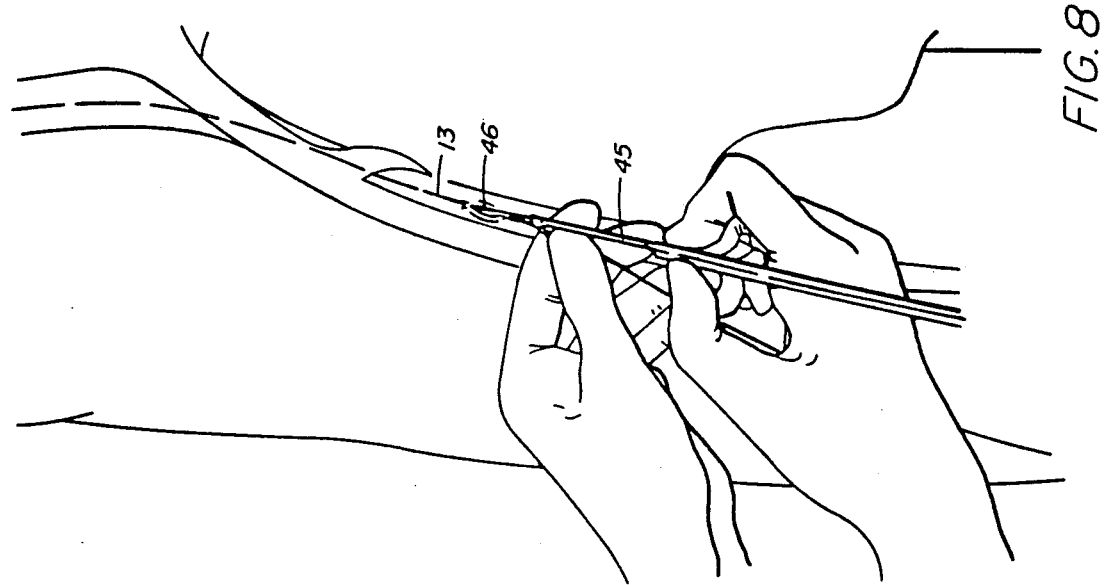

In FIG. 8, a scalpel 5 is used adjacent the wire 13 to make a small incision in the skin so that the latter will not impede the movement of the dilator sleeves.

Figure 9:
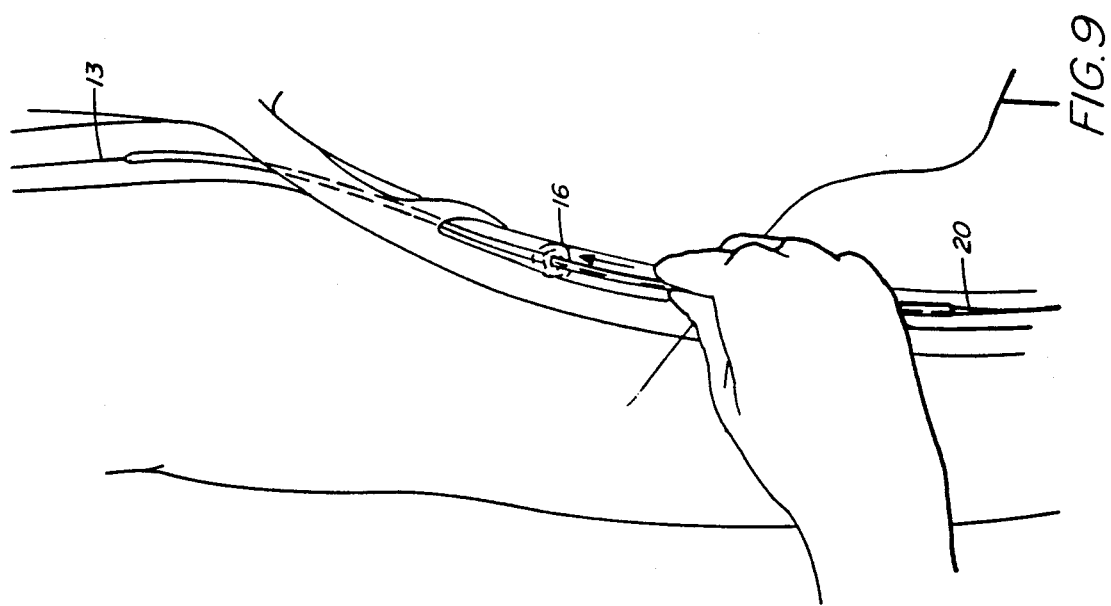

In FIG. 9, the inner dilator sleeve 16 is threaded over the wire 13 and upwardly into the vein. The tail 20 will be noted at the bottom of the Figure.

Figure 10:
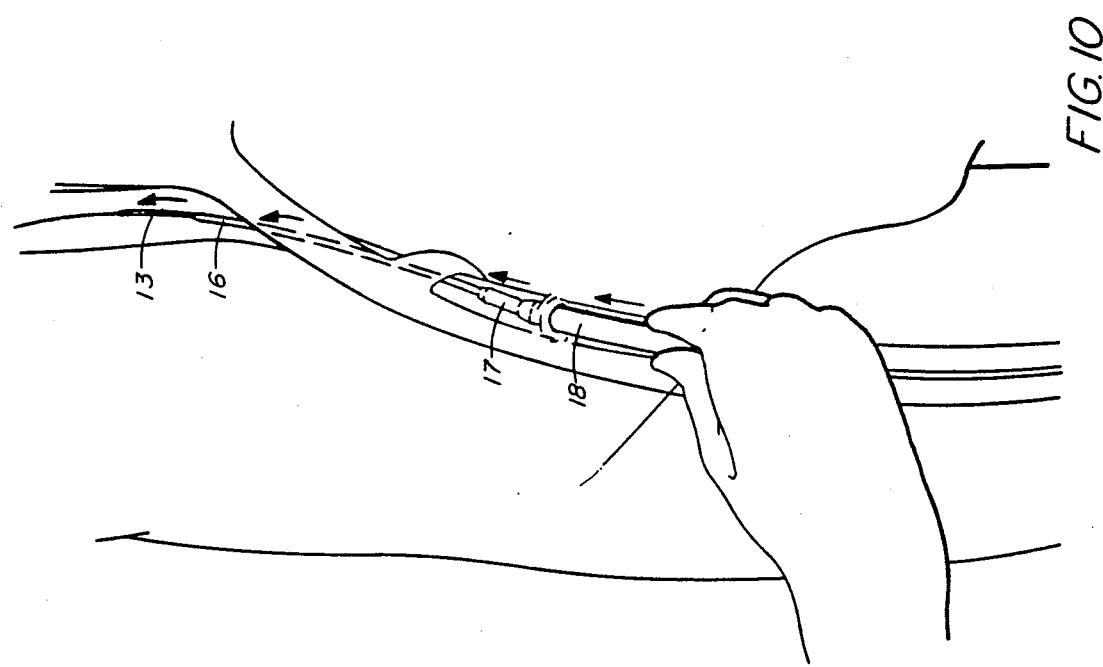

In FIG. 10, there is illustrated the progressive threading of the dilator sleeves 17, 18 and 19 over the dilator sleeve 16 and wire 13. The opening in the skin, subcutaneous tissue and the wall of the vein is thus progressively increased to the diameter of the dilator sleeve 19. In FIG. 11a, the outermost dilator sleeve 19 is shown with the sheath 24 and obturator portion 25, following the outside of the sleeve 19. The sheath 24 may be inserted with the sleeve 19, or may be inoortod separately—it is more convenient for it to be inserted with the sleeve 19 as a unit.

Figure 11B:
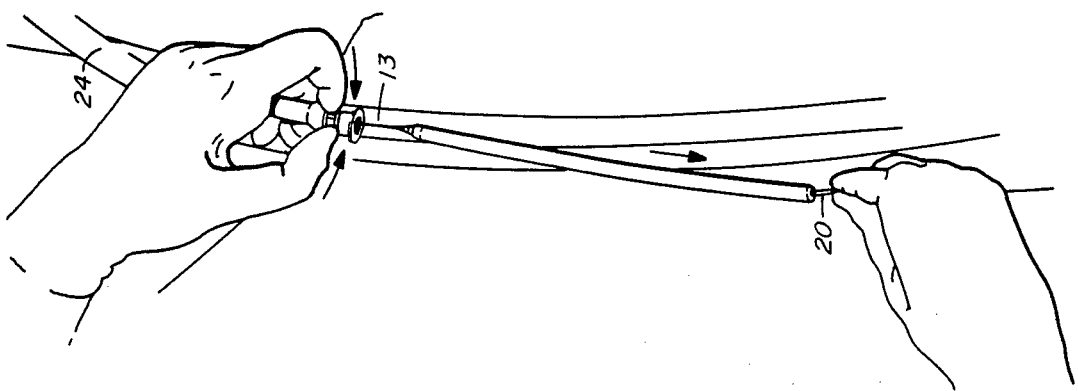
Figure 11A:
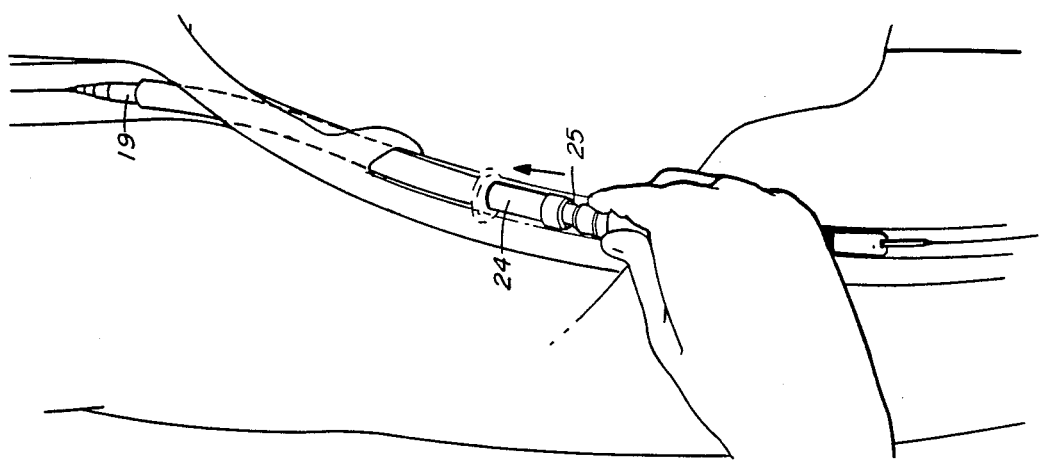

FIG. 11b illustrates the grasping of the tail by the Doctor, and the obturation by squeezing of the portion 25 of the sleeve 24. It will readily be appreciated that manipulation of the portion 25 of the sleeve 24 is quite easy, in such a manner that blood cannot escape around the wire 13 as the dilator assembly is removed.

Figure 13:
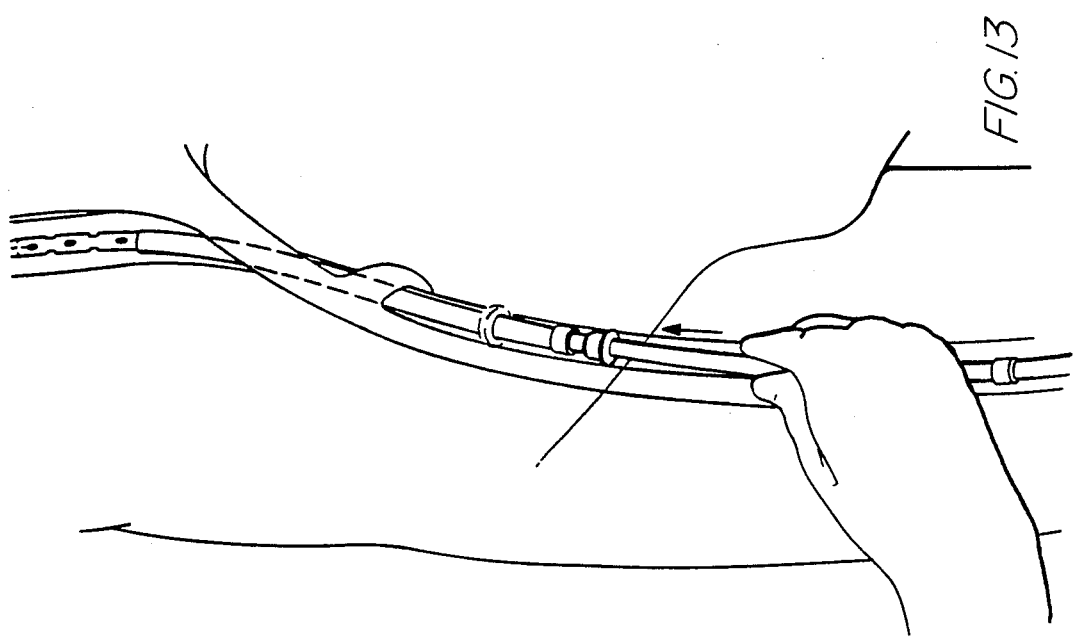
Figure 12:
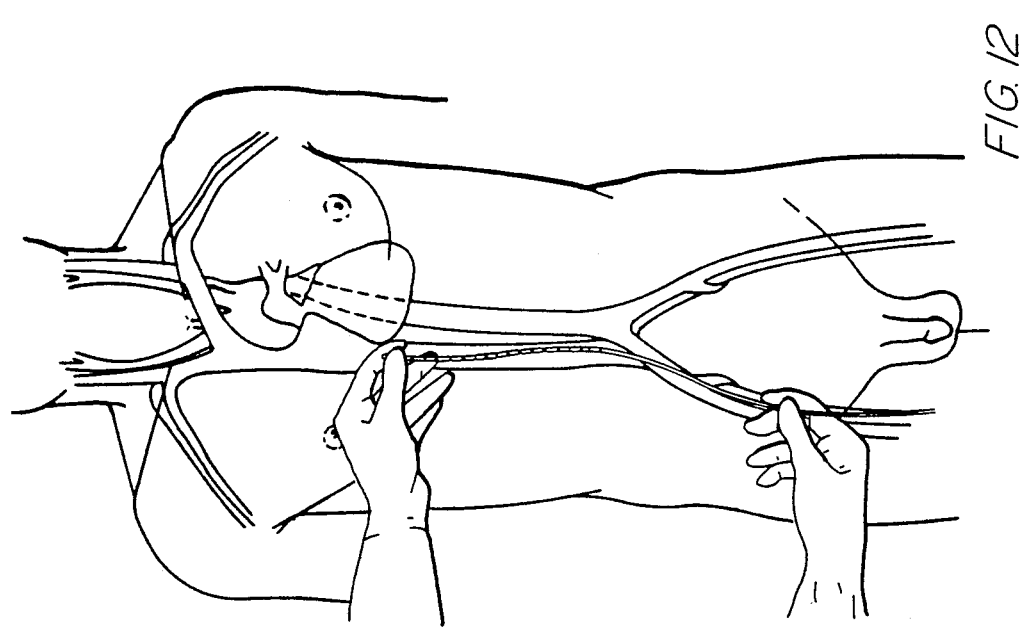
Figure 16:
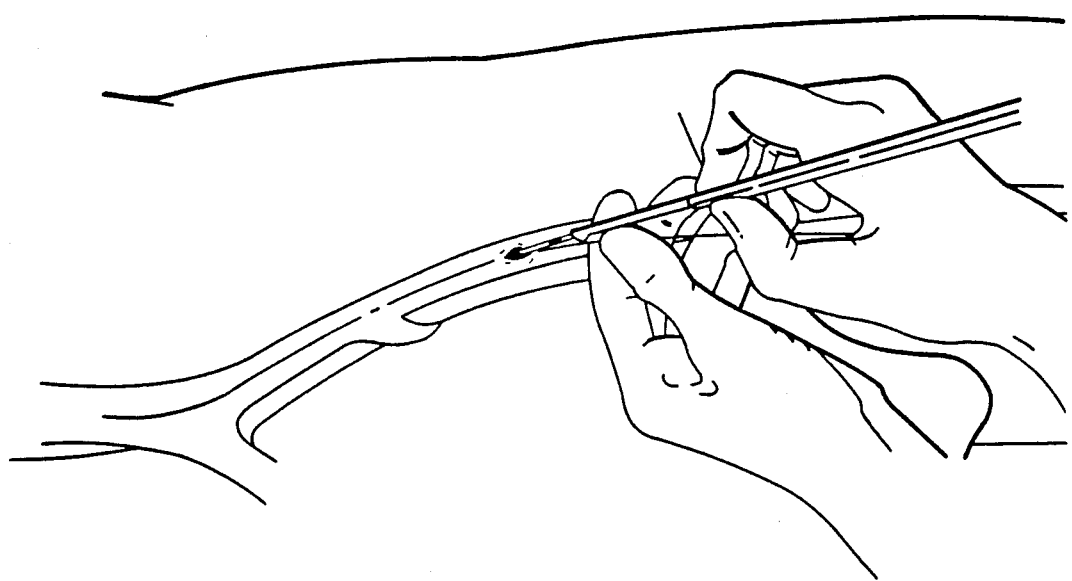
Figure 14:
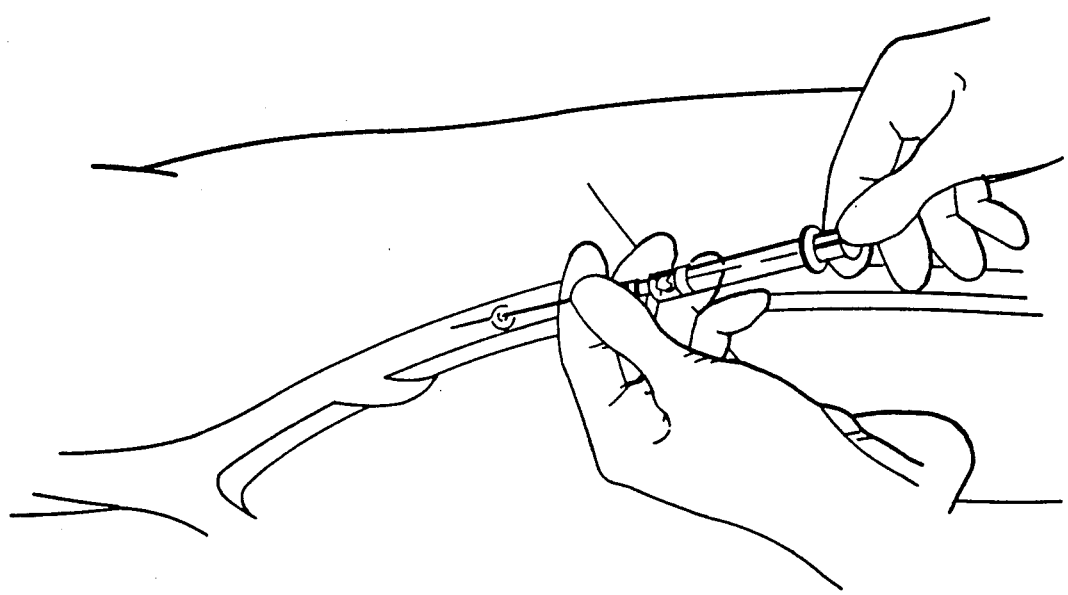
Figure 15:
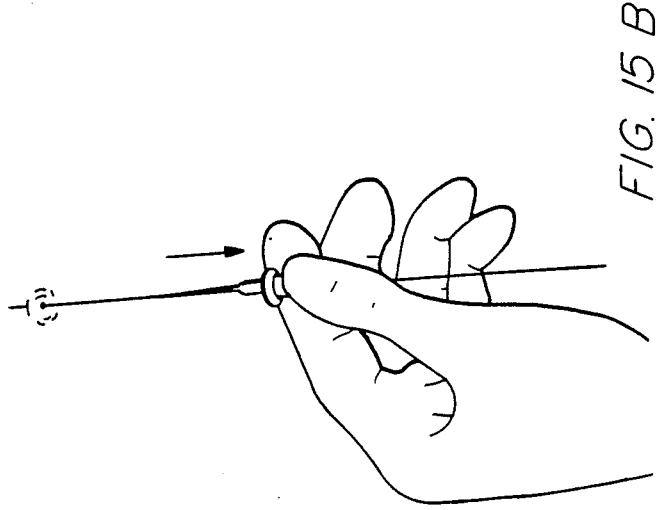
Figure 15:
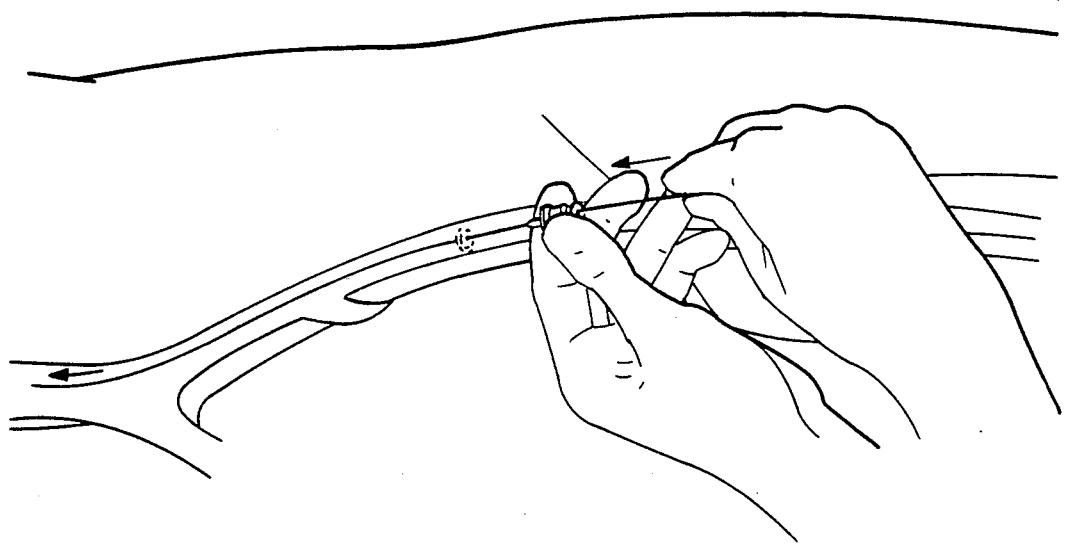
Figure 18:
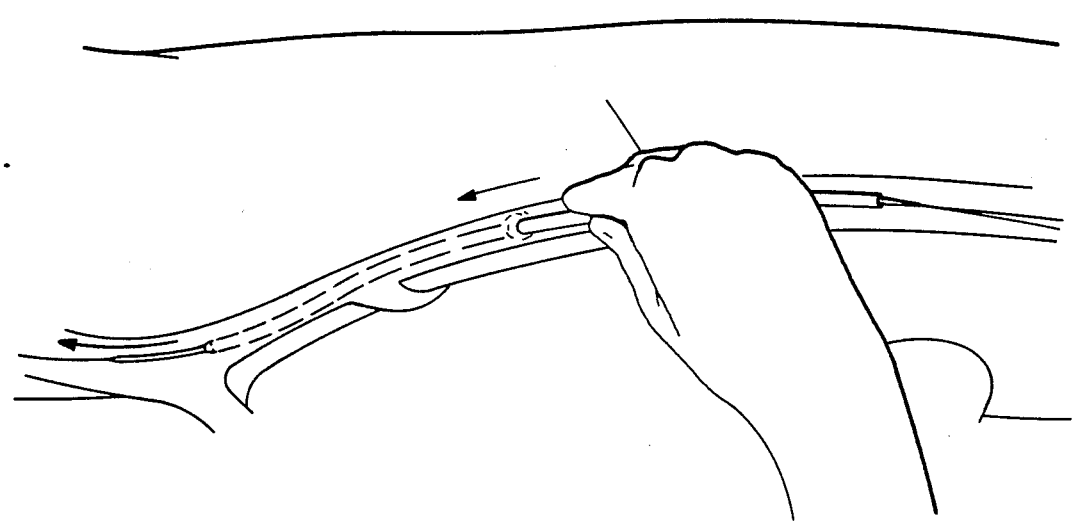
Figure 17:
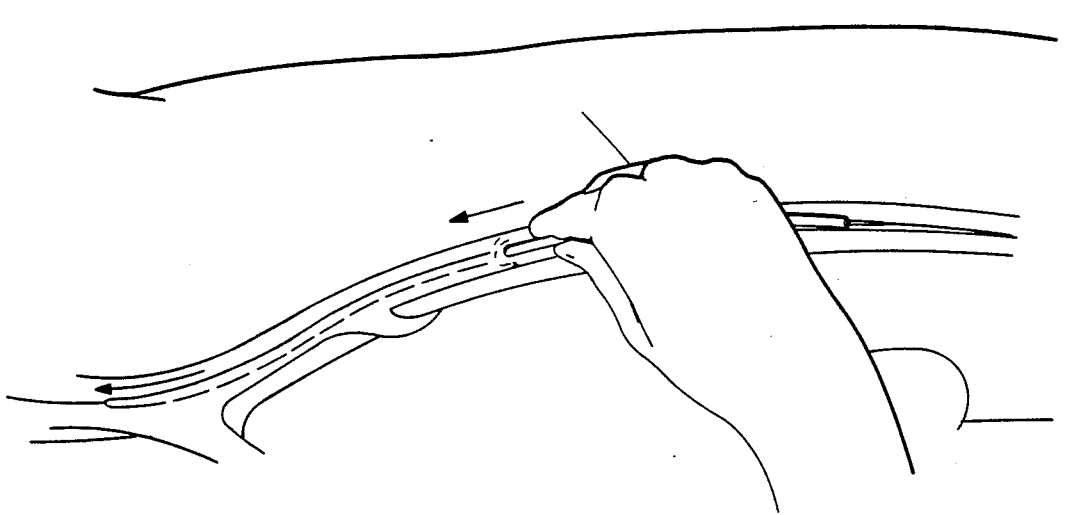
Figure 19B:
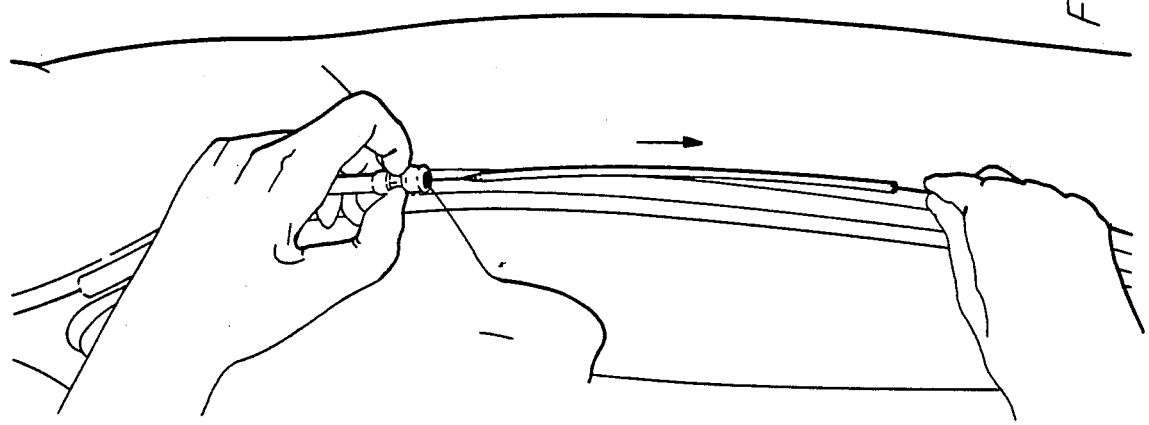
Figure 19A:
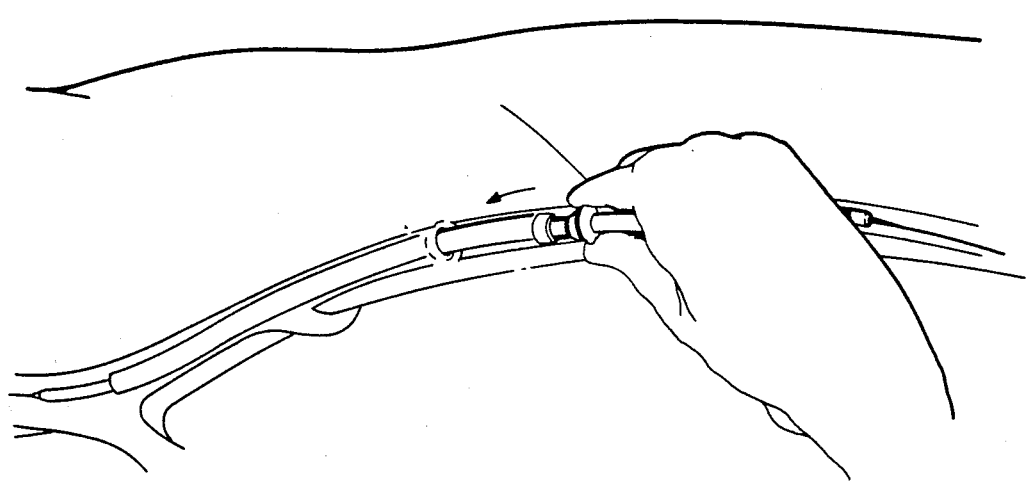
Figure 21:
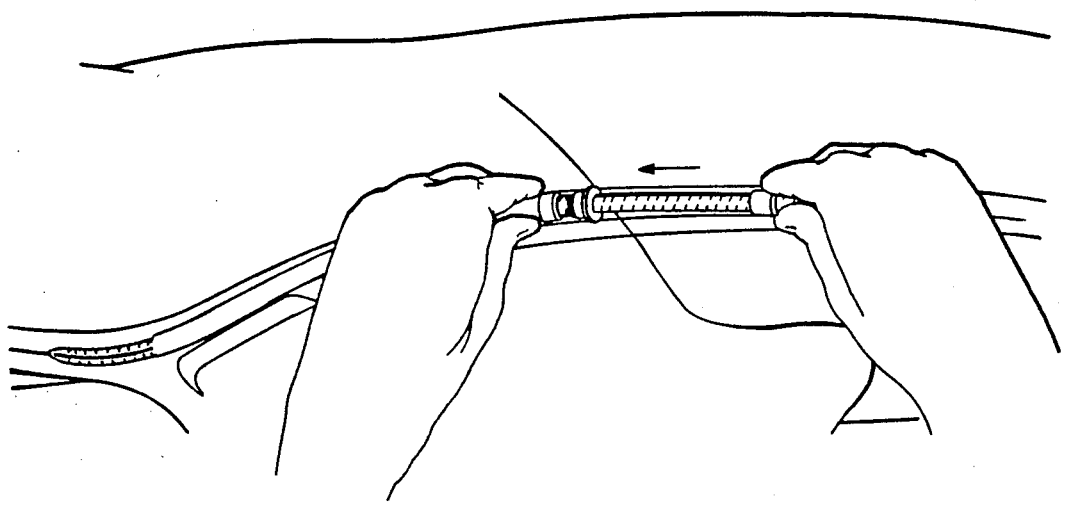
Figure 20:
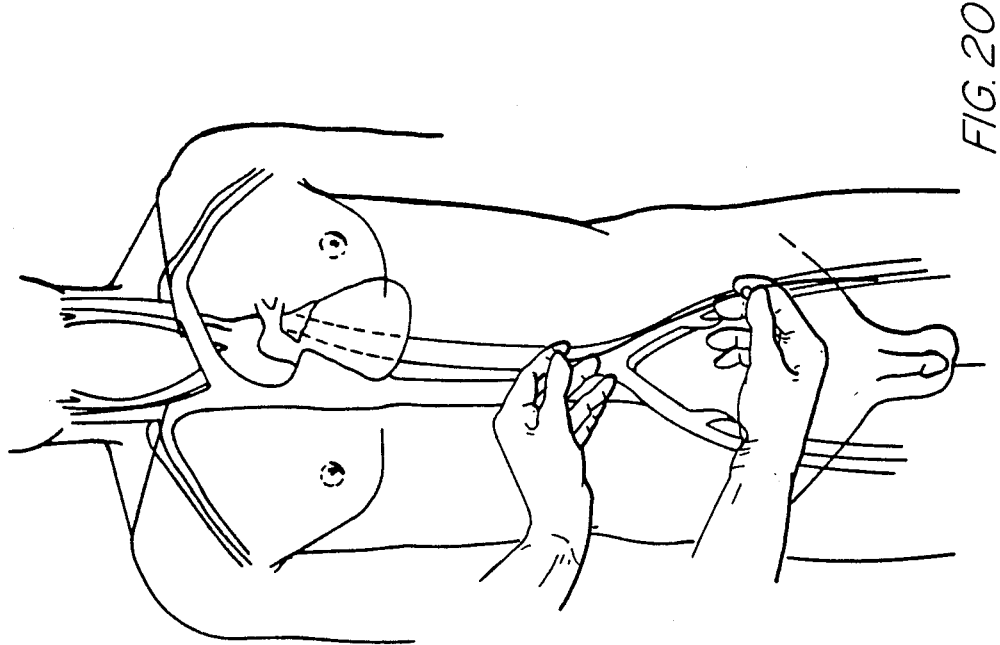
Figure 23:
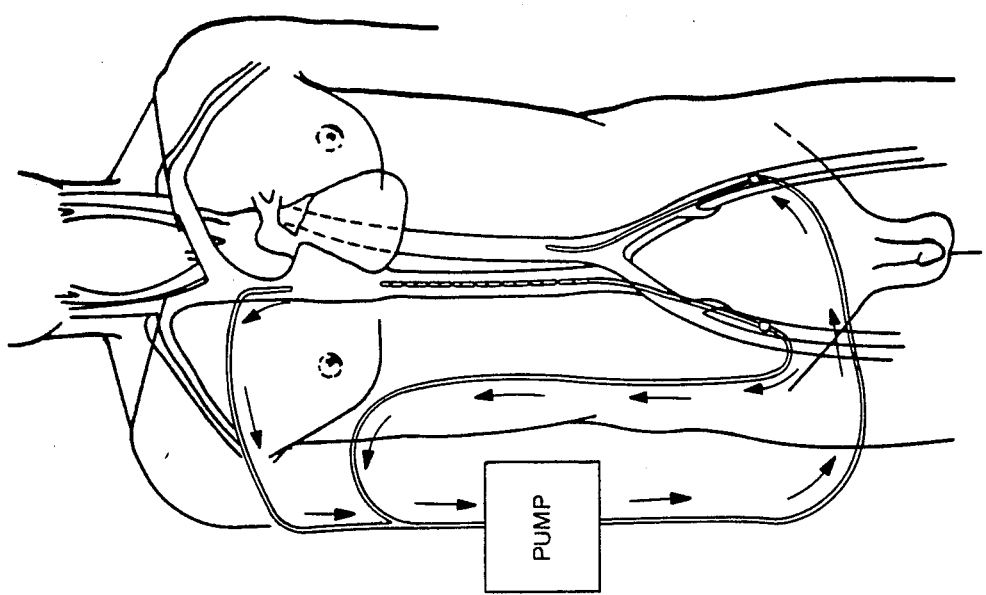

Next, in FIG. 12 prior to installation of the cannula, in this case a cannula 30 of the type having a venous drainage tip 32, the cannula is being measured for its appropriate penetration into the inferior vena cava. The Doctor has laid out the cannula over the abdomen of the patient, from a point approximately 2 inches below the nipple line to the point at which the perforation has been made in the patient's groin. The sleeve 38 shown in FIG. 5a is then moved along the cannula until the appropriate distance has been established. The cannula, with its obturator as shown in FIG. 5a, is then as illustrated in FIG. 13 inserted through the sheath 24 until the sleeve 38 reaches the sleeve. The Doctor then knows that the tip of the cannula is in its correct place, subjacent the heart. After this, as shown in FIGS. 13–21, the same series of steps is followed for insertion of an arterial cannula of the type shown in part in FIG. 5c. Again, the steps of perforating the skin and gaining access to the artery, threading of the wire, incision and insertion of dilators (FIG. 17) is followed, however, since in this case arterial pressure is met only two dilator sleeves are required to provide an opening of the appropriate diameter. Otherwise, the steps followed are the same as shown in sequence in FIGS. 18, 19a, and 20. In FIG. 20, it can be seen that the Doctor is measuring the location of the sheath by laying the cannula over the abdomen of the patient from approximately the level of his naval to the incision. The arterial cannula does not have to penetrate the artery to as great an extent as the venous cannula.

Figure 22:
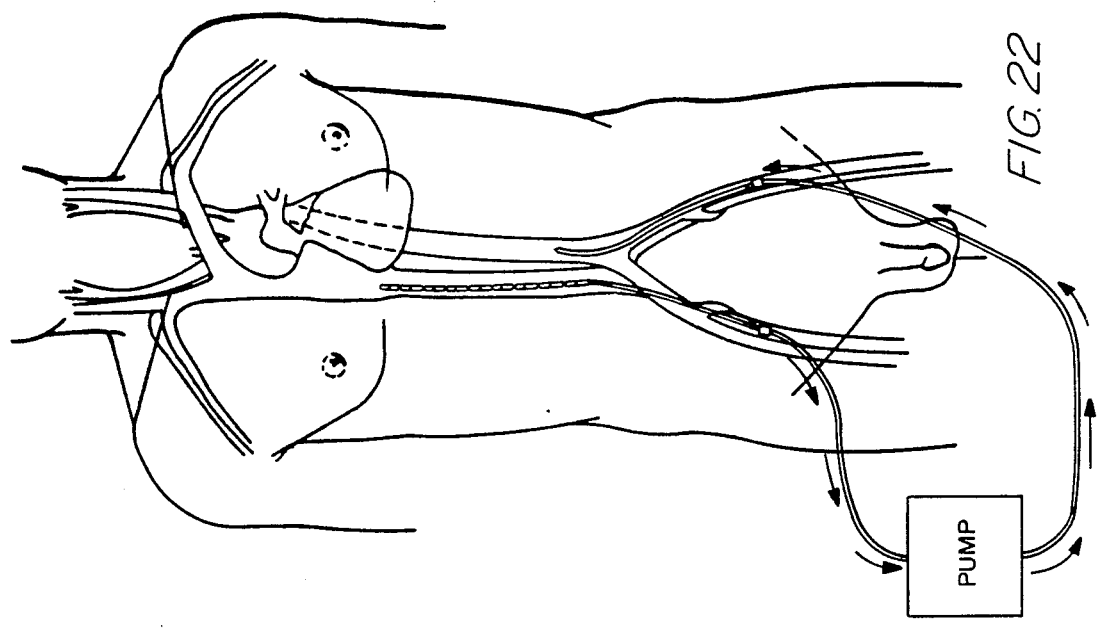

In FIG. 22, both cannulae are in place and the sleeves 38 have been slipped down the cannulae to lock into place, using conventional connectors, on tubing conveying blood from the venous system of the patient through e.g. a pump back into the arterial system for arterial support. Often, this will be preparatory to open heart surgery and it can be seem from FIG. 24 that in the event that of the patient's chest being opened for open heart surgery, an additional venous catheter is installed into the superior vena cava connected to the pump through a Y so that the blood will flow in the same direction as from the first installed cannula.

The embodiments of the invention in which an exclusive property or privilege is claimed are defined as follows:

1. A percutaneous dilator system comprising:
   (i) a first dilator tube having a tapered leading end and inwardly directed shoulder means spaced from the trailing end defining a gripping section between the shoulder and the trailing end;
   (ii) a bore through the tube dimensioned to receive a guide wire; and
   (iii) a second dilator tube having a bore corresponding to the outside diameter of the first tube, a tapered leading end, and an inwardly directed flange at the trailing end dimensioned to note with the shoulder means to limit relative axial mating movement of the first and second tubes while exposing the gripping section;

whereby a puncture through tissue containing a guide wire of predetermined gauge may be enlarged without substantial tissue damage by placing the first tube over the guide wire through the puncture, then sliding the second dilator tube over the wire and first dilator tube until its flange means engages the shoulder means to enlarge the puncture further, the dilator tubes being subsequently removable as a unit by pulling on the gripping section.

2. The system defined in claim 1 further comprising third and fourth dilator tubes corresponding in shape to the second dilator tube, with the third dilator tube dimensioned to fit over the second and the fourth dimensioned to fit over the third.

3. The system defined in claim 1 or 2 further comprising a sheath having an internal diameter dimensioned to mate with the largest dilator tube, the sheath being insertable through the puncture over said largest dilator tube to provide a guide for insertion of a cannula after removal of the dilator tubes.

4. The system defined in claim 1 or 2 or 3 further comprising an obturator forming part of the sheath so that the dilator tubes can be removed while the obturator is operated to minimize loss of bodily fluids through the sheath.

* * * * *